(12) United States Patent
Patel et al.

(10) Patent No.: US 8,133,888 B2
(45) Date of Patent: Mar. 13, 2012

(54) HYDRAZIDE CONTAINING TAXANE CONJUGATES

(75) Inventors: Jiten Ranchhodbhai Patel, Baroda (IN); Gopalkumar Chimanlal Patel, Baroda (IN); Gaurav Sanjivkumar Sheth, Baroda (IN); Trinadha Rao Chitturi, Baroda (IN); Rajamannar Thennati, Baroda (IN)

(73) Assignee: Sun Pharma Advanced Research Company Ltd., Andheri (E), Mumbai (IN)

( * ) Notice: Subject to any disclaimer, the term of this patent is extended or adjusted under 35 U.S.C. 154(b) by 0 days.

(21) Appl. No.: 12/918,985

(22) PCT Filed: Feb. 12, 2009

(86) PCT No.: PCT/IN2009/000112
§ 371 (c)(1),
(2), (4) Date: Aug. 23, 2010

(87) PCT Pub. No.: WO2010/079499
PCT Pub. Date: Jul. 15, 2010

(65) Prior Publication Data
US 2011/0172226 A1    Jul. 14, 2011

(30) Foreign Application Priority Data
Feb. 21, 2008  (IN) .......................... 378/MUM/2008

(51) Int. Cl.
| A61K 31/337 | (2006.01) |
| A61K 31/4523 | (2006.01) |
| A61K 31/5377 | (2006.01) |
| C07D 305/14 | (2006.01) |
| C07D 405/12 | (2006.01) |
| C07D 413/12 | (2006.01) |

(52) U.S. Cl. ..................... 514/232.8; 514/320; 514/449; 544/147; 546/196; 549/510

(58) Field of Classification Search .......................... None
See application file for complete search history.

(56) References Cited

U.S. PATENT DOCUMENTS
5,547,981 A * 8/1996 Greenwald et al. .......... 514/449
* cited by examiner

*Primary Examiner* — Jason M. Nolan
*Assistant Examiner* — Michael Barker
(74) *Attorney, Agent, or Firm* — Schwegman, Lundberg & Woessner, P.A.

(57) ABSTRACT

The present invention relates to compounds of formula I or salts thereof, wherein, $R_1$ is selected from the group consisting of hydrogen and $R_4$; $R_2$ is selected from the group consisting of hydrogen, acetyl and $R_4$; $R_3$ is selected from the group consisting of alkyl, —O-alkyl, —NH-alkyl, aryl and heterocyclyl; $R_4$ represents a moiety (A) wherein, X is selected from the group consisting of a single bond, alkylene, alkenylene, alkynylene, arylene or a heterocyclylene moiety; $R_5$ and $R_6$ are same or different and are independently selected from hydrogen, alkyl, aryl or heterocyclyl; or $R_5$ and $R_6$ may form together with the nitrogen atom to which they are attached a heterocyclyl ring system.

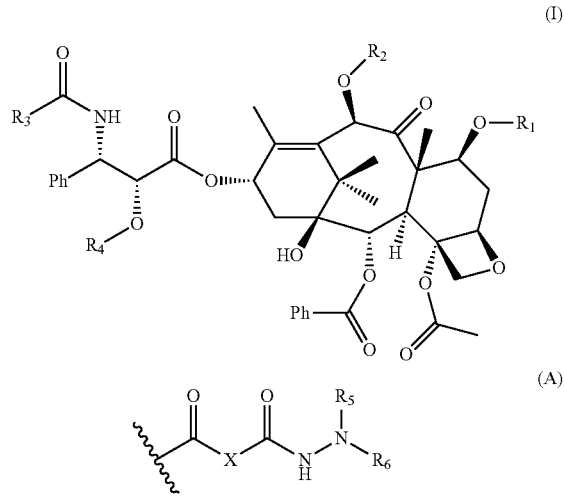

6 Claims, 2 Drawing Sheets

HYDRAZIDE CONTAINING TAXANE CONJUGATES

RELATED APPLICATIONS

This application is a U.S. National Stage Filing under 35 U.S.C. 371 from International Patent Application Serial No. PCT/IN2009/000112, filed Feb. 12, 2009, and published on Jul. 15, 2010 as WO 2010/079499 A2, which claims the priority benefit of Indian Application Serial No. 378/MUM/2008, filed Feb. 21, 2008, the contents of which applications and publication are incorporated herein by reference in their entirety.

The present invention relates to novel hydrazide containing carboxylate derivatives of taxanes and process for the preparation thereof, for use as chemotherapeutic agents in the prevention and treatment of cancer.

Formula I

BACKGROUND OF THE INVENTION

The term "Taxane" is generally referred to the diterpenes produced from plants of the genus *Taxus*. The term denotes a compound containing the core structure as in the formula below:

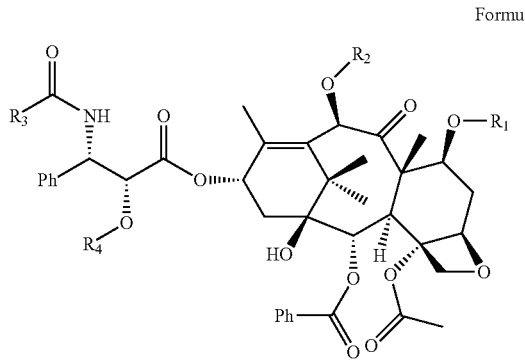

The basic taxane core structure may further be substituted or may contain unsaturations in the ring to yield a number of compounds, generically known as taxanes. The taxane group of drugs includes paclitaxel and docetaxel. Paclitaxel (Taxol®, Bristol Meyers Squibb) is a naturally occurring complex diterpenoid, which was originally isolated from the needles and bark of the Pacific yew tree (*Taxus Brevifolia*) which is a rare slow-growing tree with limited geographic distribution. The drug was discovered as part of a National Cancer Institute program in which extracts of thousands of plants and natural products were screened for anti-neoplastic activity. Later research led to semi-synthetic preparation of the drug from precursor chemicals called baccatins, which were derived from the needles and twigs of the European or Himalayan yew tree (*Taxus Bacatta*). Paclitaxel was approved in United States in December 1992 for treatment of patients with metastatic carcinoma of the ovary after failure of first-line or subsequent chemotherapy. It is currently marketed for the treatment of patients with cancer of lung, breast cancer and advanced forms of Kaposi's sarcoma.

Docetaxel (Taxotere®, Sanofi Aventis), which is reportedly the more potent congener of paclitaxel, is the first "taxoid," i.e., taxol-like compound. The main use of docetaxel is in the treatment of a variety of cancers after the failure of initial chemotherapy. It is marketed towards the treatment of breast cancer, prostate cancer, non-small cell cancer, gastric adenocarcinoma, and squamous cell carcinoma of head and neck. Clinical data has shown docetaxel to have cytotoxic activity against breast, colorectal, lung, ovarian, prostate, liver, renal and gastric cancer and melanoma cells (Lyseng-Williamson K. A., *Drugs* 2005; 65(17):2513-31). Docetaxel has been shown to improve survival as an adjuvant therapy with doxorubicin and cyclophosphamide for the treatment of node-positive breast cancer, and so docetaxel has the benefit of aiding other treatments.

Formula II below represents structure of paclitaxel ($R_1$=H; $R_2$=acetyl; $R_3$=Ph) and docetaxel ($R_1$=H; $R_2$=H; $R_3$=tert-butyloxy)

Formula II

The conventional numbering system for this class of drugs, which is also followed throughout this application is represented below:

The first-generation taxanes, paclitaxel and docetaxel, are currently considered to be two of the most exciting drugs in cancer chemotherapy. Both of these exhibit significant and broad spectrum anticancer activity against various cancers which have not been effectively treated by other chemotherapeutic drugs. The anticancer activity of these drugs is through a unique mechanism of action which involves binding reversibly to microtubules with high affinity, causing stabilization of the microtubules and preventing their depolymerization from calcium ions, decreased temperature and dilution, preferentially at the plus end of the microtubule, thereby inhibiting cell proliferations. Thus unlike other microtubule poisons such as Vinca alkaloids, colchicines, combretastatins and cryptophycins which inhibit tubulin polymerization, taxanes stabilize microtubules.

Although both paclitaxel and docetaxel have been demonstrated to be unique antitumor agents, there are several limitations to their effectiveness. These include poor selectivity for killing of cancer cells vs. normal cells, development of multidrug resistance (MDR), and poor solubility in the aqueous media which are generally employed for administered drugs. The low aqueous solubility necessitates the preparation of these drugs in non-aqueous medium, for example, a mixture of Cremophor EL® (a polyethoxylated castor oil) and ethanol as co-solvent is used in the dosage forms to solublize paclitaxel. Unfortunately, the high amount of Cremophor EL® required to deliver the indicated dose of paclitaxel exacerbates the side effects of taxol in patients. Weiss et al (*J. Clin. Oncol.,* 1990, 8, 1263-1268) and many others have reported various hypersensitive reactions which include severe skin rashes, hives, flushing, dyspnea and tachycardia in patients treated with such formulation. These effects are attributed partly due to Cremophor EL®, which is responsible for histamine release (Rowinsky, E. K. et al. *J. Natl Cancer Inst.* 1990; 82, 1247-59). Like paclitaxel, docetaxel (<0.05 mg/mL) is also poorly soluble in water. Currently used the most preferred solvent used for dissolution of docetaxel is polysorbate 80 (Tween® 80). Like Cremophor EL®, the polysorbate also, often causes hypersensitivity reactions in patients. Further, the polysorbate cannot be used with PVC delivery apparatus because of its tendency to leach toxic diethylhexyl phthalate. Thus special provisions are required for the preparation and administration of paclitaxel solutions to ensure safe drug delivery to patients, which inevitably leads to higher costs for the preparation.

Several groups have investigated the synthesis of derivatives, including prodrug forms of taxanes, with a view to improve their aqueous solubility and to develop safer clinical formulations. The studies have been directed at synthesizing taxane analogs wherein 2'- and/or 7 or 10-position is derivatized with suitable groups. These efforts yielded taxane conjugates or protaxanes of reportedly higher aqueous solubility than the parent taxane. Some of the prior art compounds are exemplified in the following references:

U.S. Pat. No. 4,942,184 (Haugwitz R. D. et al.) discloses water soluble taxols having various substituted acyl groups at 2'-O-position;

U.S. Pat. No. 4,960,790 (Stella V. J. et al.) discloses water soluble taxols, the 2' and/or 7-hydroxy of which is derivatized with a selected amino acid or an amino acid mimetic compound;

U.S. Pat. No. 5,352,805 (1994) and U.S. Pat. No. 5,411,984 (1995) (Kingston David et al.) discloses sulfonated 2'-acryloyl, sulfonated 2'-O-acyl acid taxol and substituted 2'-benzoyl and 2',7-dibenzoyl taxol which have improved water solubility;

U.S. Pat. No. 5,817,840 (1998) (Nicolaou K C et al.) discloses alkaline sensitive water soluble protaxols, protaxol composition include 2'- and/or 7-O-ester and 2'- and/or 7-O-carbonate derivatives of taxol, which have enhanced water solubility besides increased in vitro cytotoxic activity compared to paclitaxel;

U.S. Pat. No. 5,977,163 (1999) (Chun Li et al.) discloses water soluble taxane derivatives formed by conjugation with polymers such as polyethylene glycol, poly(L-glutamic acid), poly(L-aspartic acid);

PCT application published as WO9414787 (Poss M. A. et al) discloses water soluble prodrug form of taxanes possessing a phosphonoxy group at the C-7, C-10 and/or at the 2'-position of the side chain of a taxane.

Numerous other studies have also been reported in the literature with regard to conjugates of taxanes for improvement of aqueous solubility. These include:

Salts of 2'-succinylpaclitaxel and 2'-glutarylpaclitaxel, Deutsch et al. (*J. Med. Chem.* 1989, 32, 788-792);

Sulfonate derivatives—Zhao, Z. et al. (*J. Nat. Prod.* 1991, 54, 1607-1611);

2' and 7-Amino acid derivatives of paclitaxel and their salts—Mathew et al. (*J. Med. Chem.* 1992, 35, 145-151);

7-Phosphate paclitaxel analogues—Vyas et al. (*Bioorg. Med. Chem. Lett.* 1993, 3, 1357-1360);

2'- and 7-Phosphonoxyphenyl-propionate paclitaxel—Ueda, Y. et al. (*Bioorg. Med. Chem. Lett.* 1993, 3, 1761-1366);

2' and 7-Polyethylene glycol esters of paclitaxel—Greenwald et al. (*J. org. Chem.* 1995, 60, 331-336 and *J. Med. Chem.* 1996, 39, 424-431);

2'- and 7-Methylpyridinium acetate analogues of paclitaxel—Nicholaou K. C. et al. (*Angew Chemie* 1994, 106, 1672-1675) and Paloma I. G. et al. (*Chem. Biol.* 1994, 1, 107-112);

Prodrug of paclitaxel with malic acid at the 2' postion—Damen, E. W. P. et al (*Bioorg. Med. Chem. Lett.* 2000, 8, 427-432).

SUMMARY OF THE INVENTION

The present invention provides compounds of formula I or salts thereof,

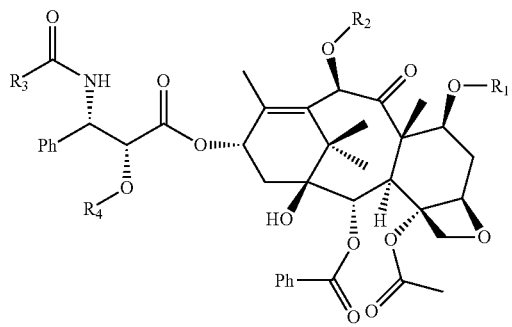

Formula I wherein, $R_1$ is selected from the group consisting of hydrogen and $R_4$;

$R_2$ is selected from the group consisting of hydrogen, acetyl and $R_4$;

$R_3$ is selected from the group consisting of alkyl, —O-alkyl, —NH-alkyl, aryl and heterocyclyl;

$R_4$ represents a moiety (A)

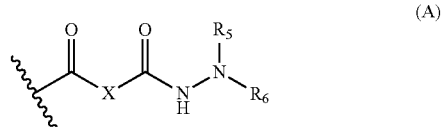

(A)

wherein, X is selected from the group consisting of a single bond, alkylene, alkenylene, alkynylene; arylene or a heterocyclylene moiety;

$R_5$ and $R_6$ are same or different and are independently selected from hydrogen, alkyl, aryl or heterocyclyl;

or $R_5$ and $R_6$ may form together with the nitrogen atom to which they are attached a heterocyclyl ring system.

DETAILED DESCRIPTION OF THE INVENTION

Figure 1:
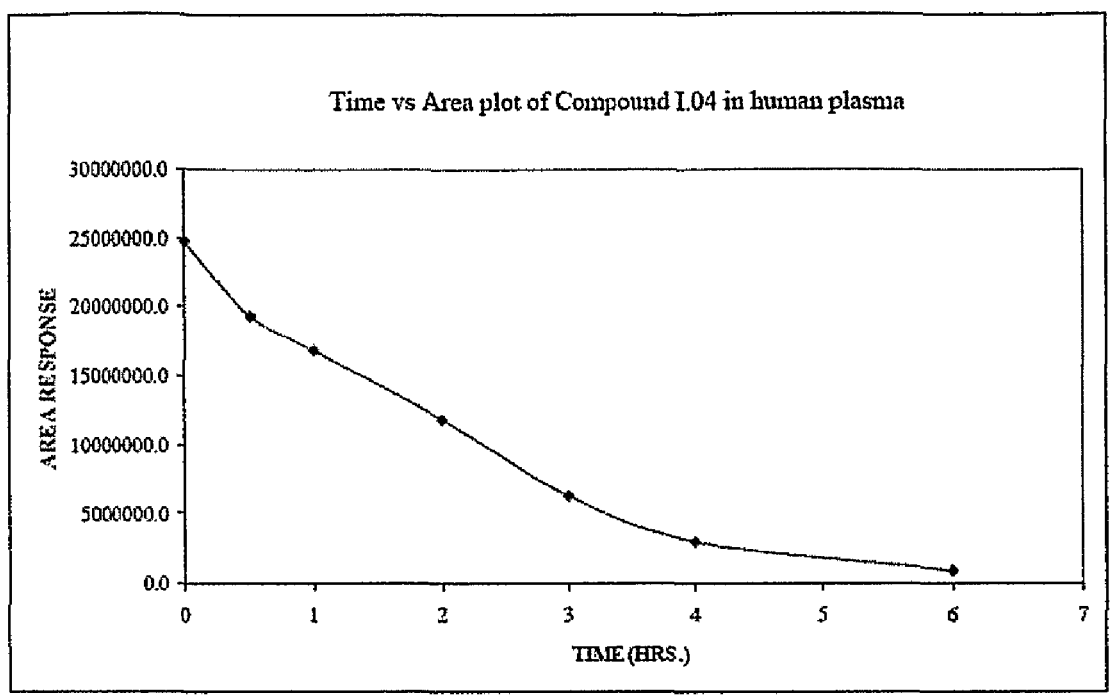
FIG. 1 depicts a time vs. area plot of compound 1.04 in human plasma.

The present invention provides compounds of formula I or salts thereof,

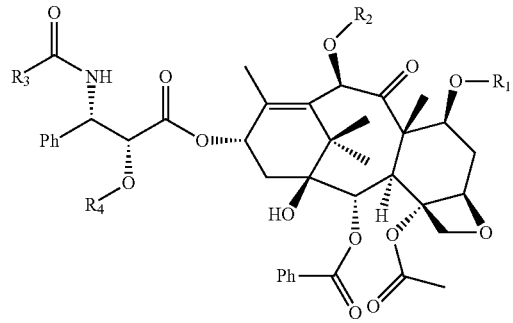

Formula I wherein, $R_1$ is selected from the group consisting of hydrogen and $R_4$;

$R_2$ is selected from the group consisting of hydrogen, acetyl and $R_4$;

$R_3$ is selected from the group consisting of alkyl, —O-alkyl, —NH— alkyl, aryl and heterocyclyl;

$R_4$ represents a moiety (A)

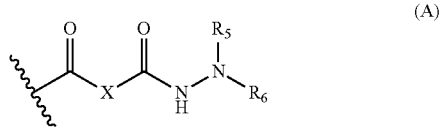

(A)

wherein, X is selected from the group consisting of a single bond, alkylene, alkenylene, alkynylene, arylene or a heterocyclylene moiety;

$R_5$ and $R_6$ are same or different and are independently selected from hydrogen, alkyl, aryl or heterocyclyl;

or $R_5$ and $R_6$ may form together with the nitrogen atom to which they are attached a heterocyclyl ring system.

The novel hydrazide group containing carboxylate derivatives of taxanes, compounds of formula I, and salts thereof have enhanced aqueous solubility.

The novel taxane conjugates of the present invention can, in general, be described as 2'-, 7- and/or 10-position ester derivatives of taxane, represented by the general formula I or salts thereof.

In one of the embodiments, the present invention relates to compounds of formula I wherein $R_1$ is hydrogen In another embodiment, the present invention relates to compounds of formula I wherein $R_1$ is hydrogen, $R_2$ is selected from hydrogen or acetyl and $R_3$ is selected from phenyl or tert-butyloxy.

The novel taxane conjugates of the present invention are more soluble in water than the taxanes of formula II, and are relatively easier to formulate and administer using aqueous infusion fluids such as sodium chloride solution, dextrose solution or a combination of these, or dextrose in Ringer's solution. The novel taxane conjugates of formula I are soluble in aqueous fluids including intravenous aqueous fluids, and are hydrolyzed under physiological conditions such as in the plasma to give the corresponding active taxane compound of formula II; the latter would have been otherwise difficult to formulate because of its insoluble nature. The compound of formula II may be represented by the structure below,

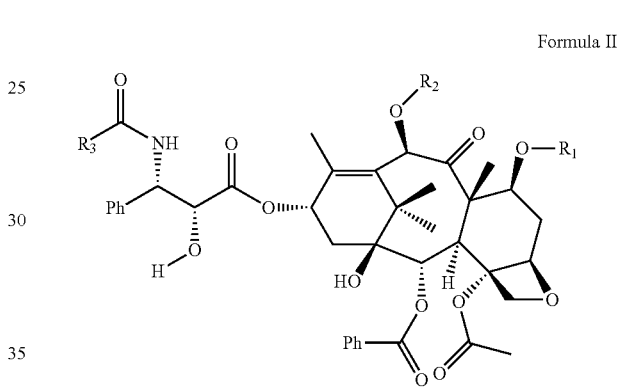

Formula II wherein, $R_1$ represents hydrogen, $R_2$ represents hydrogen or acetyl, $R_3$ represents alkyl, —O-alkyl, —NH— alkyl, aryl or heterocyclyl.

The following are the definitions of terms used in this specification. The initial definition provided for a group or term herein applies to that group or term throughout the present specification, individually or as part of another group, unless otherwise indicated.

The general terms used hereinbefore and hereinafter preferably have within the context of this disclosure the following meanings, unless otherwise indicated.

As used herein 'alkyl' can be straight-chain, branched, or cyclic aliphatic group containing 1 to 20 carbon atoms, and can optionally contain one or more unsaturations and/or can have one or more hetero atom incorporated therein and optionally, in each case have one or more hydrogen atoms replaced by halogen, —OH, alkyl, —O-alkyl, —OCO—($C_1$-$C_3$)-alkyl, ($C_3$-$C_{13}$)-cycloalkyl, —$NH_2$, —NH(alkyl), —N(alkyl)$_2$, —NH(alkyl)—OC(O)-alkyl, —OC(O)-alkyl, —($C_3$-$C_{13}$)-cycloalkyl, —SH, —S-alkyl, substituted or unsubstituted aryl or heterocyclic radical. As used herein 'alkyl including one or more unsaturations' is to be understood as meaning 'alkenyl' and/or 'alkynyl'. Exemplary alkyl groups include methyl, ethyl, n-propyl, i-propyl, n-butyl, t-butyl, n-pentyl, 3-pentyl, 2-octyl and the like. Exemplary alkenyl groups include ethenyl, propenyl, 1-butenyl, (Z)-2-butenyl, (E)-3-methylbut-2-enyl, (E)-2,4-pentadienyl, (Z)-3- heptenyl and the like. Exemplary alkynyl groups include ethynyl, propynyl, 1-butynyl, 2-butynyl, 4-methyl-2-pentynyl, 2,4-hexadiynyl and the like.

The term 'alkylene' refers to a divalent alkyl group containing 1 to 10 carbon atoms, optionally having one or more hetero atoms, arylene or heterocyclylene incorporated therein, and optionally in each case have one or more hydrogen atoms replaced by halogen, hydroxyl, alkyl, —O-alkyl, and aryl or heterocyclyl groups. Exemplary alkylene group include —$CH_2$—, —$CH(C_6H_5)CH_2$—, —$CH_2CH_2CH_2$—, —$CH_2(C_6H_4)CH_2$—, —$CH_2CH(CH_3)_2CH_2$— and the like.

The term 'alkenylene' refers to alkylene having 2 to 10 carbon atoms and having at least one double bond, the double bonds being in either E or Z configuration Exemplary alkenylene group include —CH=CH—, —$CH_2$—CH=CH—$CH_2$—, —CH=C($CH_3$)—$CH_2$— and the like.

The term 'alkynylene' refers to a divalent alkynyl group or an alkylene group containing 2 to 10 carbon atoms and having at least one triple bond. Exemplary alkynylene group include —C≡C—, —$CH_2$—C≡C—, CH($CH_3$)—C≡C—, —$CH_2$—C≡C—$CH_2$— and the like.

As used herein 'cycloalkyl' is to be understood as meaning monocyclic, bicyclic, tricyclic and polycyclic ring systems such as cyclopropyl, cyclopentyl, cyclohexyl, cycloheptyl, norbornyl, adamantyl and the like. The term 'cycloalkyl' as used herein can optionally contain one or more unsaturations and/or substitutions for e.g. halogen, —OH, —O-alkyl, —OC(O)— alkyl, ($C_3$-$C_{13}$)-cycloalkyl, aryl or heterocyclic radical.

As used herein 'halogen' or 'halo group' refers to —F, —Cl, —Br, or —I.

As used herein 'aryl' is to be understood as meaning aromatic ring systems, optionally having one or more hydrogen atoms replaced by other substitutions.

The term 'arylene' refers to an aryl-diyl group, optionally having one or more hydrogen atoms replaced by other substitutions.

As used herein 'heterocyclyl' or 'heterocyclic ring' is to be understood as meaning substituted or unsubstituted stable monocyclic or bicyclic ring systems which, in addition to carbon, also contain one or more hetero atoms, such as, for example, nitrogen, oxygen or sulfur which may be unsaturated or wholly or partly saturated. This definition furthermore includes ring systems in which the heterocyclyl rings are aromatic, i.e. 'heteroaryl'.

The heterocyyl systems containing nitrogen and sulfur heteroatoms may optionally be oxidized, and the nitrogen heteroatom may optionally be quarternized. Furthermore, the heterocyclyl radical can be fused with an aryl or a heteroaryl ring.

In substituted aryl and heterocyclic systems, the substituents that are likely to be present include halogen, —OH, —CN, —$NO_2$, -alkyl, -cycloalkyl, —O-alkyl, —O-cycloalkyl, —O-aryl, —O-heterocyclyl, -alkyl-O-alkyl, —O-alkyl-O-alkyl, —O-alkyl-NH(alkyl), —O-alkyl-N(alkyl)$_2$, —O-alkyl-(heterocyclyl), —C(O)-alkyl, —COON, —C(O)$NH_2$, —C(O)NH-alkyl, —C(O)N(alkyl)$_2$, —C(O)O-alkyl, -haloalkyl, -alkenyl, -alkynyl, —OC(O)—$NH_2$, —OC(O)—NH(alkyl), —OC(O)—N(alkyl)$_2$, —$NH_2$, —NH(alkyl), —N(alkyl)$_2$, —NH—$SO_2$-alkyl, N(alkyl)-$SO_2$-alkyl, —NH—C(O)-(alkyl)-N(alkyl)-C(O)-alkyl, —NH—C(O)O-alkyl, —N(alkyl)-C(O)O-alkyl, —NH—C(O)—$NH_2$, —NH—C(O)—NH(alkyl), —N(alkyl)-C(O)—NH(alkyl), —N(alkyl)-C(O)—N(alkyl)$_2$, —NH—C(O)—NH—$SO_2$-alkyl, —N(alkyl)-C(O)—NHSO$_2$— alkyl, —N(alkyl)-C(O)—N(alkyl)-$SO_2$-alkyl, —S-alkyl, —S(O)-alkyl, —$SO_2$-alkyl, —S-aryl, —S(O)-aryl, $SO_2$-aryl, —S-heterocyyl, —SO-heterocyyl, —$SO_2$-heterocyyl, —$SO_2NH_2$, —$SO_2$NH-(alkyl), —$SO_2$N(alkyl)$_2$, heterocyclyl and an aryl group in each case are unsubstituted or mono- or polysubstituted.

Heterocyclyl is especially a five, six or seven-membered ring system with one or two heteroatoms for e.g. 2-piperazinyl, 2- or 3-pyrrolidinyl, 2-oxo-5-pyrrolidinyl, piperidinyl, N-benzyl-4-piperidinyl, N-alkyl-4-piperidinyl, N-alkyl-piperazinyl, morpholinyl, e.g. 2- or 3-morpholinyl, 2-oxo-1H-azepin-3-yl, 2-tetrahydrofuranyl, or 2-methyl-1,3-dioxolan-2-yl.

Examples of heteroaryl rings are benzimidazolyl, 1-[($C_1$-$C_6$)-alkyl]benzimidazolyl, imidazolyl, 2- or 3-thienyl, 2- or 3-furyl, benzoxazolyl, benzothiazolyl, 2-, 3- or 4-pyridyl, pyrimidinyl, 4-, 5- or 6-pyridazin-2H-yl-3-one, 4-, 5- or 6-pyridazin-2-($C_1$-$C_8$)-alkyl-2H-yl-3-one, 2-benzyl-4-, -5- or -6-pyridazin-2H-yl-3-one, 3- or 4-pyridazinyl, 2-, 3-, 4- or 8-quinolinyl, 1-, 3- or 4-isoquinolinyl, 1-phthalazinyl, 3- or 4-cinnolinyl, 2- or 4-quinazolinyl, 2-pyrazinyl, 2-quinoxalinyl, 2-, 4- or 5-oxazolyl, 3-, 4- or 5-isoxazolyl, 2-, 4- or 5-thiazolyl, 3-, 4- or 5-isothiazolyl, 1-[($C_1$-$C_6$)-alkyl]-2-, -4- or -5-imidazolyl, 3-, 4- or 5-pyrazolyl, 1-[($C_1$-$C_6$)-alkyl]-3-, -4- or -5-pyrazolyl, 1- or 4-[1,2,4]-triazolyl, 4- or 5-[1,2,3]-triazolyl, 1-[($C_1$-$C_6$)-alkyl]-4- or -5-[1,2,3]triazolyl, 3-, 4- or 7-indolyl, N—[($C_1$-$C_6$)-alkyl]-3-, -4- or -7-indolyl, 2-[($C_1$-$C_6$)-alkyl]-3(2H)-indazolyl, 1-[($C_1$-$C_6$)-alkyl]-3 (1H)-indazolyl, 5-tetrazolyl, 1-[($C_1$-$C_6$)-alkyl]-1H-tetrazolyl, 2-[($C_1$-$C_6$)-alkyl]-2H-tetrazolyl.

The term 'heterocyclylene' refers to a heterocyclyl-diyl group, optionally having one or more hydrogen atoms replaced by halogen, alkyl, —O-alkyl, aryl or heterocyclyl groups, for example pyridin-3,5-diyl, imidazol-2,4-diyl, thiazol-2,5-diyl, benzimidazol-1,6-diyl, pyrimidin-2,4-diyl etc.

With the groups of preferred compounds of formula I and N-oxides thereof mentioned hereinafter, definitions of substituents from the general definitions mentioned hereinbefore may reasonably be used, e.g. to replace more general definitions with more specific definitions or especially with definitions characterized as being preferred.

Any asymmetric carbon atom may be present in the (R)—, (S)— or (R,S)-configuration. The compounds may thus be present as mixtures of isomers or as pure isomers.

The invention relates also to possible tautomers of the compounds of formula I.

Where the plural form is used for compounds, salts and the like, this is taken to mean also a single compound, salt, or the like.

Salts are especially the pharmaceutically acceptable salts of compounds of formula I. Such salts are formed, e.g. as acid addition salts, preferably with organic or inorganic acids or from compounds of formula I with a basic nitrogen atom, especially the pharmaceutically acceptable salts. Suitable inorganic acids are, e.g. halogen acids, such as hydrochloric acid, sulfuric acid or phosphoric acid. Suitable organic acids are, e.g. carboxylic, phosphonic, sulfonic or sulfamic acids, e.g. acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, benzoic acid, salicylic acid, 4-aminosalicylic acid, phthalic acid, mandelic acid, cinnamic acid, benzenesulfonic acid, 2-naphthalenesulfonic acid, 1,5-naphthalene-disulfonic acid, 2-, 3- or 4-methylbenzenesulfonic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, e.g. sodium, potassium, magnesium or calcium salts, or ammonium salts with ammonia or suitable organic amines, such as tertiary monoamines, e.g. erbumine or tris(2-hydroxyethyl)amine, or heterocyclic bases, e.g. N-ethylpiperidine or N,N'-dimethylpiperazine.

When an acid group is present in the same molecule, the compound of formula I may also form internal salts.

For isolation or purification purposes it is also possible to use pharmaceutically unacceptable salts, e.g. picrates or perchlorates. For therapeutic use, only pharmaceutically acceptable salts or free compounds are employed and these are therefore preferred.

In view of the close relationship between the novel compounds in free form and those in the form of their salts, including those salts that can be used as intermediates, e.g. in the purification or identification of the novel compounds, any reference to the free compounds hereinbefore and hereinafter is to be understood as referring also to the corresponding salts, as appropriate and expedient.

The compounds of the present invention can be exemplified by the following non-limiting examples:

| Compound | Chemical Name |
|---|---|
| I.01 | 2'-[N-(N,N-Dimethylamino)succinamidoyl]taxol |
| I.02 | 10-Deacetyl-N-debenzoyl-N-(tert-butyloxycarbonyl)-2'-[(N-morpholin-4-yl)succinamidoyl]taxol |
| I.03 | 10-Deacetyl-N-debenzoyl-N-(tert-butyloxycarbonyl)-2',7-bis[(N-piperidin-1-yl)succinamidoyl]taxol |
| I.04 | 10-Deacetyl-N-debenzoyl-N-(tert-butyloxycarbonyl)-2'-[(N-piperidin-1-yl)succinamidoyl]taxol |
| I.05 | 10-Deacetyl-N-debenzoyl-N-(tert-butyloxycarbonyl)-2'-[[5-methyl-3-(piperidin-1-ylcarbamoyl)methyl] hexanoyl]taxol |
| I.06 | 10-Deacetyl-N-debenzoyl-N-(tert butyloxycarbonyl)-2'-[4-(piperidin-1-ylcarbamoyl)butyryl]taxol |
| I.07 | 10-Deacetyl-N-debenzoyl-N-(tert-butyloxycarbonyl)-2'-[3,3-dimethyl-4-(piperidin-1-ylcarbamoyl)butyryl]taxol |
| I.08 | 2'-[3-(N-(piperidin-1-yl)-carbamoyl)benzoyl]taxol |
| I.09 | 2'-[(Z)-3-(Piperidin-1-ylcarbamoyl)acroyl] taxol |
| I.10 | 2'-[(N-Piperidin-1-yl)succinamidoyl]taxol |

The present invention provides process for the preparation of the compounds of formula I, which comprises reacting the compound of formula II with a compound of formula III (Scheme-I).

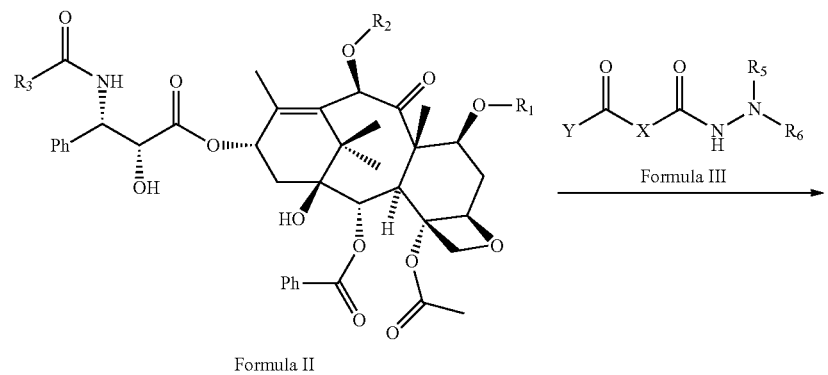

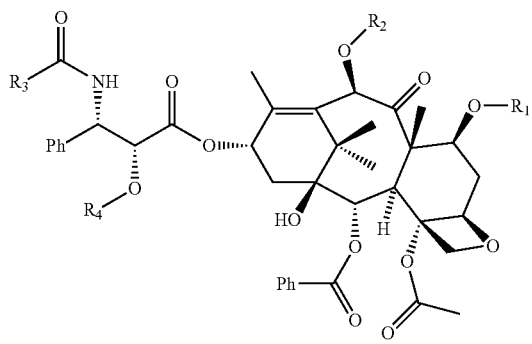

Formula I

In compounds of formula II and formula III, $R_1$, $R_2$, $R_3$, $R_4$, $R_5$, $R_6$ and X are as defined above for formula I. In activated form of formula III, Y is a leaving group, and the condensation reaction is performed preferably in the presence of an inert base and/or a suitable catalyst in an inert solvent. The compound of formula III in activated form can alternatively be generated in situ from the corresponding acid (Y=OH) and then condensed with the compound of formula II to generate the compound of formula I. Compounds of formula III, wherein Y=OH may be prepared by a process known in the art, for example, by condensation of the corresponding dicarboxylic acid of the general formula X—(COOH)$_2$, or its mono ester, or a cyclic anhydride of the general formula X—(CO)$_2$O with a suitable hydrazine derivative, H$_2$N—NR$_5$R$_6$.

A compound of the formula III in activated form is especially an acyl halide (Y=halo), a reactive ester, a reactive anhydride or a reactive cyclic amide. The method of preparation of such activated derivatives form the corresponding acid is, in general, known in the art. For example, activated form of formula III wherein Y is a halide can be obtained for example by treatment of the corresponding acid with a halogenating agent such as thionyl chloride, phosphorus pentachloride or oxalyl chloride.

The reactive esters of the acid of formula III may be for example, esters unsaturated at the linking carbon atom of the esterifying radical, for example esters of the vinyl ester type, such as actual vinyl esters, which may be obtained, for example, by transesterification of a corresponding ester with vinyl acetate; or carbamoylvinyl esters, which may be obtained, for example, by treatment of the corresponding acid with an isoxazolium reagent like 1,2-oxazolium; or 1-alkoxyvinyl esters, which may be prepared, for example, by treatment of the corresponding acid with an alkoxyacetylene;

esters of the amidino type, such as N,N'-disubstituted amidino esters, which may be obtained for example, by treatment of the corresponding acid with a suitable N,N'-disubstituted carbodiimide, for example, N,N'-dicyclohexylcarbodiimide or by treatment of the corresponding acid with N,N-disubstituted cyanamide;

suitable aryl esters, especially phenyl esters suitably substituted by electron withdrawing substituents, which may be obtained, for example, by treatment of the corresponding acid with a suitably substituted phenol, for example, 4-nitrophenol, 4-methylsulfonylphenol, in presence of a condensation agent, such as N,N'-dicyclohexylcarbodiimide;

cyanomethyl esters, which may be prepared, for example, by treatment of the corresponding acid with chloroacetonitrile in the presence of a base;

thioesters, for example, nitro-substituted, phenylthioesters which may be obtained, for example, by treatment of the corresponding acid with nitro-substituted, thiophenols, or inter alia by the anhydride or carbodiimide method;

amino or amido esters which may be obtained, for example, by treatment of the corresponding acid with an N-hydroxyamino or N-hydroxyamido compound, for example, N-hydroxysuccinimide, N-hydroxypiperidine, N-hydroxyphthalimide or 1-hydroxybenzotriazole, for example by the anhydride or carbodiimide method.

The reactive anhydrides of the acid of formula III may be symmetric or preferably mixed anhydrides such as, anhydrides with carbonic acid semiderivatives, for example carbonic acid alkyl semiesters, which may be obtained, for example, by treatment of the corresponding acid with haloformic, such as chloroformic, acid, alkyl esters or with a 1-alkoxycarbonyl-2-alkoxy-1,2-dihydroquinoline, for example 1-alkoxycarbonyl-2-ethoxy-1,2-dihydroquinoline;

anhydrides with organic acids, such as mixed anhydrides with organic carboxylic acids (obtainable, for example, by treatment of the corresponding acid with an unsubstituted or substituted alkane acid halide, for example, pivalic acid chloride or trifluoroacetyl chloride);

anhydrides with organic sulfonic acids (obtainable, for example, by treatment of a salt, such as an alkali metal salt, of the corresponding acid, with a suitable organic sulfonic acid halide, for example methane- or p-toluenesulfonyl chloride);

anhydrides with organic phosphonic acids (obtainable, for example, by treatment of the corresponding acid with a suitable organic phosphonic anhydride or phosphonic cyanide), or anhydrides with dihalogenated phosphoric acid which may be obtained, for example, by treatment of the corresponding acid with phosphorus oxychloride.

The symmetric anhydrides may be obtained, for example, by condensation of the corresponding acid in the presence of a carbodiimide or of 1-(diethylamino)propyne.

Suitable cyclic amides may be amides with five-membered aromatic compounds with two nitrogen atoms, such as amides with imidazoles, obtainable, for example, by treatment of the corresponding acid with N,N'-carbonyldiimidazole; or pyrazoles, for example 3,5-dimethylpyrazole (obtainable, for example, by way of the acid hydrazide by treatment with acetylacetone).

Formula III in activated form is preferably generated in situ from the corresponding acid (Y=OH). For example, N,N'-disubstituted amidino esters can be formed in situ by reacting a mixture of the acid of formula III (Y=OH) and the compound of formula II in the presence of a suitable condensating agent for example N,N'-dicyclohexylcarbodiimide. Reactive mixed anhydrides of the acid of formula III (Y=OH) may also be generated with an organic phosphonic acid in situ by reaction with propylphosphonic anhydride or diethylcyanophosphonate in the presence of suitable base for e.g. triethylamine or 4-(dimethylamino)pyridine.

The reaction can be carried out in a manner known per se, the reaction conditions being dependent especially on how the acid group of formula III (Y=OH) has been activated, usually in the presence of a suitable solvent or diluent or of a mixture thereof and, if necessary, in the presence of a condensation agent. Customary condensation agents are, for example, carbodiimides such as N,N'-diethyl-, N,N'-diisopropyl, N,N'-dicyclohexyl- or N-ethyl-N'-(3-diethylaminopropyl)-carbodiimide; suitable carbonyl compounds, for example carbonyldiimidazole, or 1,2-oxazolium compounds, for example 2-ethyl-5-phenyl-1,2-oxazolium-3'-sulfonate and 2-tert-butyl-5-methyl-isoxazolium perchlorate, or a suitable acylamino compound, for example, 2-ethoxy-1-ethoxycarbonyl-1,2-dihydroquinoline. The bases normally used for aiding the condensation are either inorganic bases such as sodium or potassium carbonate, or organic bases, such as pyridine, triethyamine, N,N'-diisopropyl-N-ethylamine or 4-(dimethylamino)pyridine.

Alternatively, the compounds of formula I can be synthesized using a compound of formula IV, wherein Y is a leaving group and the compound is in activated form, the substituents $R_1, R_2, R_3, R_4, R_5, R_6$, X are as defined above. The compound of formula IV can be generated in situ from the corresponding acid i.e. Y=OH, which in turn can be prepared from the compound of formula II by methods known to those skilled in the art. Activated compounds of formula IV can be prepared using acid of formula IV, wherein Y=OH, in a manner similar to that for compounds of formula III as described vide supra in detail. The activated compound thus obtained may be subsequently condensed with the hydrazine compound of formula V to obtain the required hydrazide compound of formula I (Scheme II). Compounds of formula V may be prepared from the corresponding amines using processes generally known in the art for the preparation of hydrazines. For example, the desired hydrazine of formula V may be prepared from the corresponding amine by nitrosation/diazotization and subsequent reduction using reducing agents like zinc-acid, sodium bisulfite, by catalytic hydrogenation etc.

Scheme-II

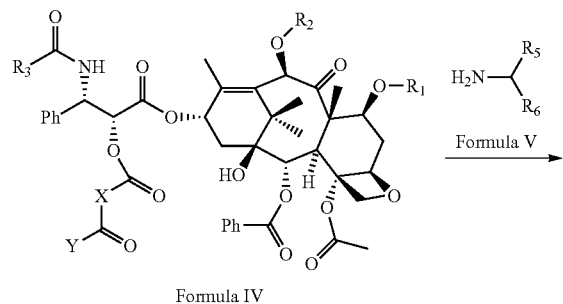

Formula IV

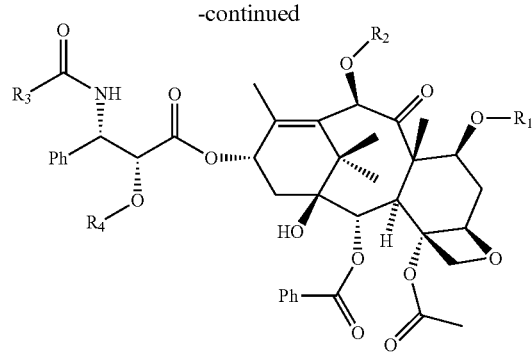

Formula I

The compound of formula I may be isolated in crude form by methods known to those skilled in the art. Final purification may be carried out by chromatography, including preparative chromatography, recrystallization, or by other methods known to those skilled in the art such as acid-base purification, solvent leaching etc.

The compounds of formula I wherein 7- and/or 10-position are also derivatized besides the 2'-position with —OR$_4$ may be prepared from the corresponding compounds of formula I possessing —OH group at these positions.

The compounds of formula II, used as a starting material for the reaction, are either known in the art and commercially available or can be prepared by following known methods, for example, Wani, M. C.; Wall, M. E., J. Chem. Soc. 93, 2325 (1971); Kingston, D. G. I., J. Org. Chem. 62, 3775-78 (1997), European Patent No. 253, 738, U.S. Pat. No. 4,814,470, which is incorporated herein by reference.

The compounds of formula I, including their salts, are also obtainable in the form of hydrates.

The compounds of formula I release the parent taxane under physiological conditions, which then binds to the microtubules reversibly with high affinity. The binding of the taxane to the microtubule stabilizes microtubules and prevents depolymerization induced by microtubule disrupting agents like calcium chloride, thereby inhibiting cell proliferations. Thus, the taxanes exhibit a unique mechanism of action in that, they promote the assembly of microtubules but inhibit their disassembly, thereby interfering with the G2 and M phases of cell division. Accordingly, the novel taxane conjugates of the present invention may be utilized in the treatment of a disease which responds to an inhibition of microtubule depolymerization, more preferably in the treatment of cancer. More preferably, the compounds of formula I of the present invention are useful in the prophylactic or especially therapeutic management of cancer. Furthermore, the compounds of formula I are useful for the treatment of other warm-blooded animals. Such a compound may also be used as a reference standard in the test systems, to permit a comparison with other compounds.

For use in therapy, a compound of formula I or a salt thereof may be administered in a therapeutically effective amount to a patient in need. The term "therapeutically effective amount" refers to a sufficient amount of compound of formula I or salt thereof, which is effective for prophylactic and/or therapeutic treatment of a condition caused due to inhibition of microtubule depolymerization, especially, for treatment of cancer, in a mammal in need thereof, at a reasonable benefit/risk ratio applicable to any medical treatment. The specific therapeutic effective dose level for any particular patient will depend upon a variety of factors including the type of cancer being treated, the stage or the severity of the disease, the activity of the compound employed, the specific pharmaceutical preparation employed, the individual pharmacokinetic data and the mode of administration of the active ingredient.

Furthermore, the compounds of formula I may be administered for tumor therapy either separately, or in addition to radiotherapy, immunotherapy, surgical intervention or a combination of these. The compounds may be administered as a part of long-term therapy or as adjuvant therapy in the context of other treatment strategies, as described above. Other possible treatments may include therapy to maintain the patient's status after remission or tumor regression, or even chemopreventive therapy, e.g. in patients at risk.

A compound of formula I can be administered alone or in combination with one or more other therapeutic agents, possible combination therapy taking the form of fixed combinations, or the administration of a compound of the invention and one or more other therapeutic agents being staggered or given independently of one another, or the combined administration of fixed combinations and one or more other therapeutic agents.

Therapeutic agents for possible combination are especially another tyrosine kinase inhibitors such as imatinib, nilotinib, sorafenib, lapatinib, sunitinib, gefitinib, erlotinib, one or more cytostatic or cytotoxic compounds, e.g. a chemotherapeutic agent or several selected from the group comprising indarubicin, cytarabine, interferon, hydroxyurea, busulfan, DNA alkylating/intercalating agent, an inhibitor of polyamine biosynthesis, antifolate agent, topoisomerase I & II inhibitor, proteosome inhibitor, an inhibitor of protein kinase, especially of serine/threonine protein kinase, such as protein kinase C, or of tyrosine protein kinase, such as epidermal growth factor receptor tyrosine kinase, a cytokine, a negative growth regulator, such as TGF-β or IFN-β, an aromatase inhibitor, classical cytostatic, and an inhibitor of the interaction of an SH2 domain with a phosphorylated protein The compounds of the present invention may be administered in the form of a suitable pharmaceutical preparation, for example, as parenteral preparations, to a warm-blooded animal in need thereof. The pharmaceutical preparation may comprise the active ingredient alone, or preferably, together with a pharmaceutically acceptable carrier. The pharmaceutical preparation may comprise from approximately 1% to approximately 95% active ingredient for a single-dose administration. Suitable pharmaceutical preparations may be solutions of the active ingredient, especially isotonic aqueous solutions, dispersions or suspensions which, for example in the case of lyophilized compositions comprising the active ingredient alone or together with a carrier can be made up before use. The pharmaceutical preparation may comprise pharmaceutically acceptable carriers such as stabilizers, wetting agents and/or emulsifiers, solubilizers, salts for, regulating osmotic pressure and/or buffers etc. Further, the preparations may be prepared in a manner known per se, for example by means of conventional dissolving and lyophilizing processes. The said solutions or suspensions may optionally contain viscosity-increasing agents or solubilizers. For sterile preparations, they may be subjected to end-stage sterilization and/or may contain excipients to prevent microbial contamination, for example preservatives.

The following examples serve to illustrate the invention without limiting the invention in its scope.

EXAMPLE 1

2'-[N—(N,N-Dimethylamino)succinamidoyl]taxol
(Compound I.01)

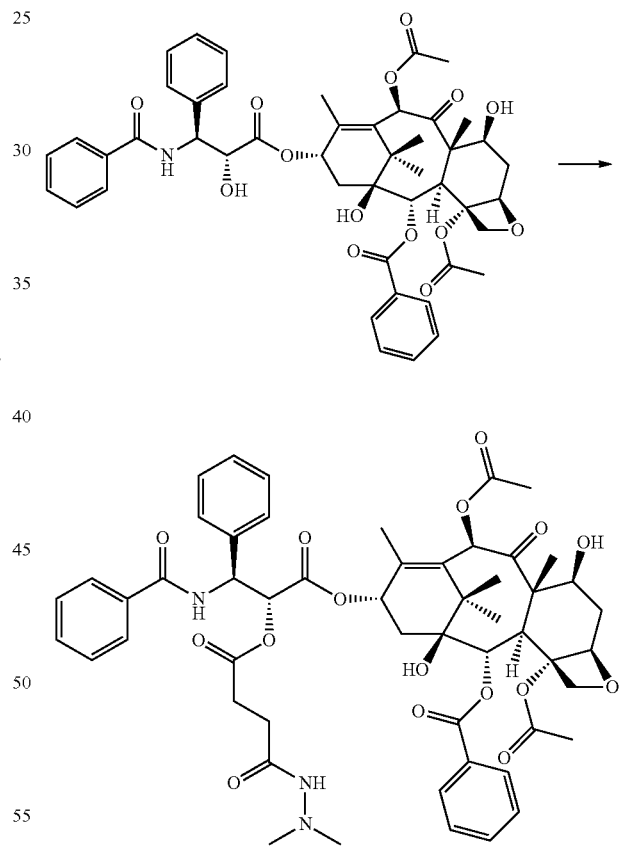

A mixture of paclitaxel (0.30 g, 0.35 mmol), 3-(N',N'-dimethylhydrazinocarbonyl)-propionic acid (0.112 g, 0.70 mmol), 1,3-dicyclohexylcarbodiimide (0.181 g, 0.87 mmol) and 4-(dimethylamino)pyridine (0.042 g, 0.35 mmol) in anhydrous methylene chloride (20 ml) was stirred under a blanket of nitrogen at ambient temperature for 4 hrs. The mixture was cooled to −15° C. and filtered to remove the precipitated dicyclohexylurea.

Filtrate was washed with water, dried, and concentrated in vacuo. The residue was purified by flash chromatography on silica gel (100% ethyl acetate) to yield the title compound as a white solid, m.p. 157-161° C.

Compounds I.08, I.09 & I.10 were synthesized in a manner analogous to compound I.01.

EXAMPLE 2

10-Deacetyl-N-debenzoyl-N-(tert-butyloxycarbonyl)-2'-[(N-morpholin-4-yl)succinamidoyl]taxol (Compound I.02)

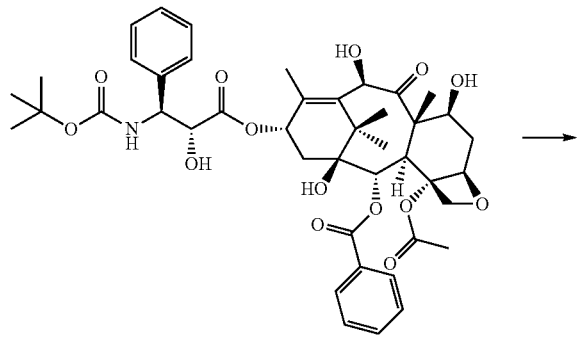

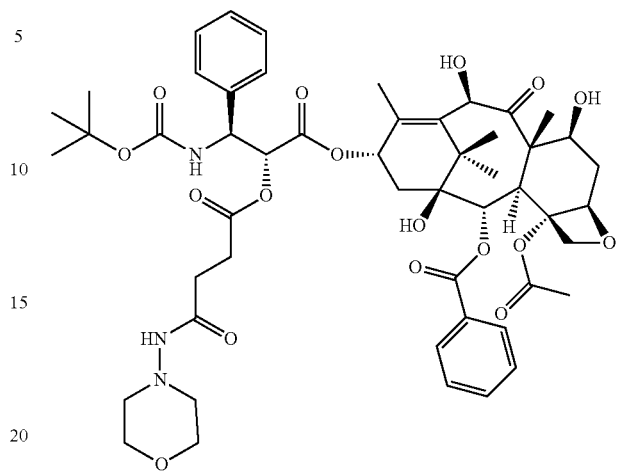

A mixture of docetaxel (0.500 g, 0.61 mmol), N-morpholin-4-yl-succinamic acid (0.250 g, 1.23 mmol), 1-ethyl-3-[3-(dimethylamino)propyl]carbodiimide hydrochloride (0.296 g, 1.54 mmol) and 4-(dimethylamino)pyridine (0.070 g, 0.61 mmol) in anhydrous methylene chloride (20 ml) was stirred under a blanket of nitrogen at 25-30° C. for 6.0 hrs. The reaction mixture was quenched with water; the organic layer was separated, washed with water, dried and concentrated in vacuo. The residue was purified by flash chromatography on silica gel (40% acetone in hexane) to yield the title compound as a white solid, m.p. 155-157° C.

Compounds I.05, I.06 & I.07 were synthesized in an analogous manner.

EXAMPLE 3

10-Deacetyl-N-debenzoyl-N-(tent-butyloxycarbonyl)-2',7-bis[(N-piperidin-1-yl)succinamidoyl]taxol (Compound I.03)

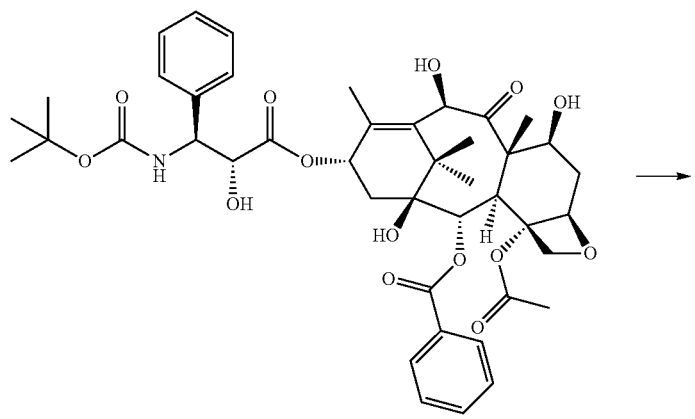

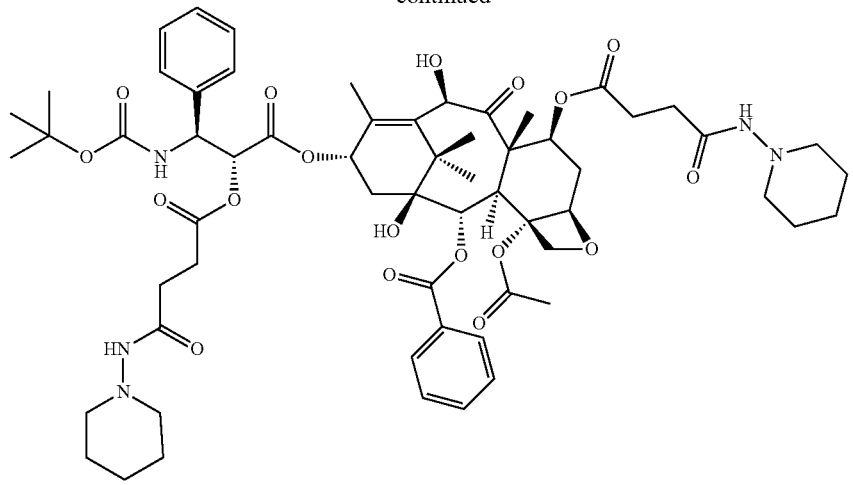

A mixture of docetaxel (2.0 g, 2.47 mmol), N-piperidin-1-yl-succinamic acid (1.98 g, 9.9 mmol) 1,3-dicyclohexylcarbodimide (1.53 g, 7.4 mmol), 4-(dimethylamino)pyridine (032 g, 2.4 mmol) in anhydrous methylene chloride (50 ml) was stirred under a blanket of nitrogen at 25-30° C. for 3.5 hrs. The reaction mixture was cooled to 5° C. and filtered to remove the precipitated dicyclohexylurea. The filtrate was washed with water, dried, concentrated in vacuo and the residue was purified by preparative HPLC (acetonitrile-water gradient, ODS Shimpack Column) to yield the title compound as a white solid, m.p 136-138° C.

The compound I.04 was also prepared and purified in a manner similar to that of compound I.03, however docetaxel, N-piperidin-1-yl-succinamic acid, 1,3-dicyclohexylcarbodimide, 4-(dimethylamino)pyridine taken were in the mole ratios of 1.0:1.1:2.0:0.5.

EXAMPLE 4

10-Deacetyl-N-debenzoyl-N-(tert-butyloxycarbonyl)-2'-[(N-piperidin-1-yl)-succinamidoyl]taxol (Compound I.04)

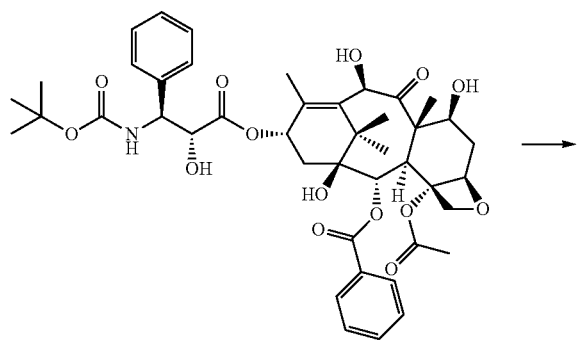

A mixture of docetaxel (2.0 g, 2.47 mmol), 4-(dimethylamino)pyridine (0.302 g, 2.47 mmol), succinic anhydride (0.495 g, 4.95 mmol) and dry pyridine (10 ml) was stirred under a blanket of nitrogen at 25-30° C. for 5.5 hrs. Citric acid solution, 30 ml (50% in water) was added to the reaction mixture to produce an off-white precipitate. The product was extracted into ethyl acetate, the ethyl acetate layer washed with water, dried, and concentrated in vacuo to yield the 2'-succinoyldocetaxel as an off-white solid, m.p. 126-130° C.

(Benzotriazol-1yloxy)tris(dimethylamino)phosphonium hexafluorophosphate (BOP) (1.16 g, 2.64 mmol) was added to a stirred solution containing 2'-succinoyldocetaxel (1.2 g, 1.32 mmol), triethylamine (0.36 ml, 2.64 mmol) and 1-aminopiperidine (0.198 g, 1.98 mmol) in anhydrous methylene chloride (50.0 ml). The mixture was stirred under a blanket of nitrogen at 25 to 30° C. for 6 hrs and then poured into water. The organic layer was separated, washed with water, dried, and concentrated in vacuo. The residue was purified by column chromatography on silica gel (50% acetone in hexane) to yield the title compound as a white solid, m.p. 195-198° C.

Table-1 and Table-2 illustrate respectively the chemical structures, and the proton NMR & mass spectrometric data of the representative examples.

TABLE 1

Representative compounds of formula I

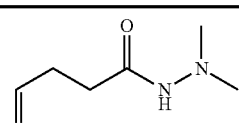

Formula I

| Comp No. | $R_1$ | $R_2$ | $R_3$ | $R_4$ | Chemical Name |
|---|---|---|---|---|---|
| I.01 | H | COCH$_3$ | Phenyl | 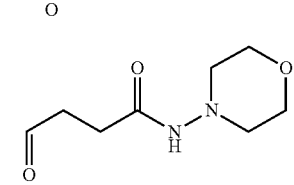 | 2'-[N-(N,N-Dimethylamino)-succinamidoyl]taxol |
| I.02 | H | H | t-Butyloxy | 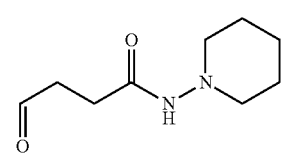 | 10-Deacetyl-N-debenzoyl-N-(tert-butyloxycarbonyl)-2'-[(N-morpholin-4-yl)succinamidoyl]taxol |
| I.03 | 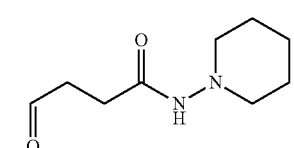 | | H | t-Butyloxy | 10-Deacetyl-N-debenzoyl-N-(tert-butyloxycarbonyl)-2',7-bis[(N-piperidin-1-yl)succinamidoyl]taxol |
| I.04 | H | H | t-Butyloxy | 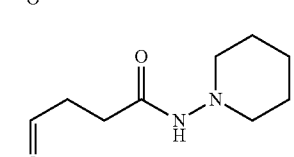 | 10-Deacetyl-N-debenzoyl-N-(tert-butyloxycarbonyl)-2'-[(N-piperidin-1-yl)succinamidoyl]taxol |
| I.05 | H | H | t-Butyloxy | 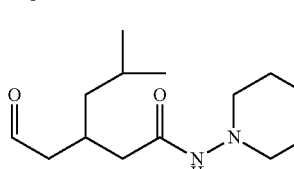 | 10-Deacetyl-N-debenzoyl-N-(tert-butyloxycarbonyl)-2'-[[5-methyl-3-(piperidin-1-ylcarbamoyl)methyl]hexanoyl]taxol |
| I.06 | H | H | t-Butyloxy | 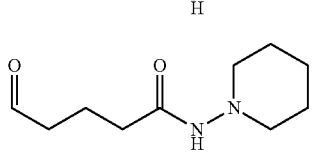 | 10-Deacetyl-N-debenzoyl-N-(tert-butyloxycarbonyl)-2'-[4-(piperidin-1-yl-carbamoyl)butyryl]taxol |
| I.07 | H | H | t-Butyloxy | 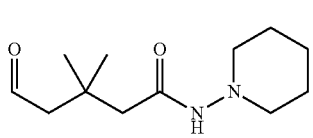 | 10-Deacetyl-N-debenzoyl-N-(tert-butyloxycarbonyl)-2'-[3,3-dimethyl-4-(piperidin-1-ylcarbamoyl)butyryl]taxol |

TABLE 1-continued

Representative compounds of formula I

Formula I

| Comp No. | $R_1$ | $R_2$ | $R_3$ | $R_4$ | Chemical Name |
|---|---|---|---|---|---|
| I.08 | H | COCH$_3$ | Phenyl | | 2'-[3-(N-(piperidin-1-yl)-carbamoyl)benzoyl]taxol |
| I.09 | H | COCH$_3$ | Phenyl | | 2'-[(Z)-3-(Piperidin-1-ylcarbamoyl)acroyl]taxol |
| I.10 | H | COCH$_3$ | Phenyl | | 2'-[(N-Piperidin-1-yl)succinamidoyl]taxol |

TABLE 2

Spectral data for the synthesized compounds

| Comp. No | $^1$H-NMR (δ ppm), mass (ES+, m/z) |
|---|---|
| I.01 | 1.21(s, 3H), 1.31(s, 3H), 1.53(s, 3H), 1.76(s, 3H), 1.93-1.99(m, 1H), 2.00(s, 3H), 2,18-2.33(m, 1H), 2.28(s, 3H), 2.39-2.48(m, 2H), 2.48(s, 3H), 2.51(s, 3H), 2.59-2.69(m, 2H), 2.83-2.87(m, 4H), 3.90(d, J = 7.05 Hz, 1H), 4.30(d, J = 8.46 Hz, 1H), 4.36(d, J = 8.46 Hz, 1H), 4.47-4.51(m, 1H), 5.01-5.02(m, 1H), 5.58(d, J = 3.45 Hz, 1H), 5.76(d, J = 7.06 Hz, 1H), 5.82(br-s, 1H), 6.04(d, J = 6.15 Hz, 1H), 6.30(t, J = 8.68 Hz, 1H), 6.39(s, 1H), 7.17(m, 1H), 7.36-7.39 (m, 1H), 7.45-7.48(m, 6H), 7.53-7.59(m, 3H), 7.66(t, J = 7.35 Hz, 1H), 7.87(d, J = 7.20 Hz, 2H), 8.21(d, J = 7.50 Hz, 2H). MASS: 996.59 |
| I.02 | 1.12(s, 3H), 1.22(s, 3H), 1.33(s, 9H), 1.63-1.70(m, 1H), 1.74(s, 3H), 1.81-1.87(m, 2H), 1.93(s, 3H), 2.14-2.37(m, 3H), 2.41(s, 3H), 2.54-2.84(m, 8H), 3.48-3.80(m, 4H), 3.91(d, J = 6.18 Hz, 1H), 4.17-4.26(m, 4H), 4.32(d, J = 8.37 Hz, 1H), 4.94(s, 1H), 4.97-5.50(m, 3H), 5.68(d, J = 6.72 Hz, 1H), 6.20(s, 1H), 7.29-7.38(m, 5H), 7.51(t, J = 7.44 Hz, 2H), 7.61(t, J = 7.18 Hz, 1H), 8.11(d, J = 7.42 Hz, 2H). MASS: 992.12 |
| I.03 | 1.12(s, 3H), 1.20(s, 3H), 1.34(s, 9H), 1.63(m, 12H), 1.81(s, 3H), 1.96(s, 3H), 2.27-2.37(m, 6H), 2.42(s, 3H), 2.50-2.55(m, 3H), 2.62-2.82(m, 8H), 3.04(m, 3H), 3.98-3.99(br-s, 1H), 4.19(d, J = 8.25 Hz, 1H), 4.32(d, J = 8.26 Hz, 1H), 4.41(s, 1H), 4.95(d, J = 8.56 Hz, 1H), 5.28(s, 1H), 5.32(s, 1H), 5.40-5.56(m, 4H), 5.67(d, J = 6.45 Hz, 1H), 6.10-6.16(m, 2H), 7.30-7.38(m, 5H), 7.51(t, J = 7.33 Hz, 2H), 7.61(t, J = 7.01 Hz, 1H), 8.11(d, J = 7.41 Hz, 2H). MASS: 1172.69 |
| I.04 | 1.10(s, 3H), 1.16(s, 3H), 1.25(s, 3H), 1.28-1.42(m, 2H), 1.38(s, 9H), 1.66-1.71(m, 6H), 1.71(s, 3H), 1.82-1.89(m, 4H), 2.36(s, 3H), 2.19-2.47(m, 3H), 2.71-2.74(m, 4H), 3.29(s, 1H), 3.82(t, J = 6.39 Hz, 1H), 4.17-4.29(m, 1H), 4.18(d, J = 8.17 Hz, 1H), 4.25(d, J = 8.38 Hz, 1H), 4.31-4.32(m, 1H), 4.69(d, J = 7.1 Hz, 1H), 4.94(d, J = 8.84 Hz, 1H), 5.20-5.25(m, 3H), 5.61(d, J = 5.39 Hz, 1H), 6.05-6.15(m, 1H), 6.31-6.33(d, J = 9.22 Hz, 1H), 7.24-7.40(m, 5H), 7.51-7.55(m, 3H), 8.09(d, J = 7.59 Hz, 2H). MASS: 990.3 |
| I.05 | 0.82-0.91(m, 6H), 1.11-1.29(m, 8H), 1.33(s, 9H), 1.60-1.75(m, 14H), 1.85-2.05(s, 6H), 2.31-2.44(m, 10H), 2.56-3.01(m, 4H), 3.93-3.94(s, 1H), 4.19-4.34(m, 4H), 4.97(d, J = 7.24 Hz, 1H), 5.21(d, J = 7.96 Hz, 1H), 5.27-5.78(m, 3H), 6.08-6.26(m, 2H), 6.65(s, 1H), 7.29-7.41(m, 5H), 7.51-7.61(m, 3H), 8.11-8.13(m, 2H). MASS: 1060.67 |

TABLE 2-continued

Spectral data for the synthesized compounds

| Comp. No | $^1$H-NMR (δ ppm), mass (ES+, m/z) |
|---|---|
| I.06 | 1.12(s, 3H), 1.22(s, 3H), 1.33(s, 9H), 1.64-1.72(m, 1H), 1.75(s, 3H), 1.82-1.91(m, 4H), 1.96(s, 3H), 2.18-2.63(m, 8H), 2.44(s, 3H), 2.74-2.99(m, 2H), 3.93(d, J = 6.35 Hz, 1H), 4.19(d, J = 7.33 Hz, 1H), 4.26-4.31(m, 1H), 4.32(d, J = 8.38 Hz, 1H), 4.96(s, 1H), 5.21(s, 1H), 5.32-5.70(m, 4H), 6.08-6.50(m, 3H), 7.29-7.31(m, 3H), 7.38(t, J = 6.82 Hz, 2H), 7.51(t, J = 7.54 Hz, 2H), 7.61(t, J = 7.31 Hz, 1H), 8.11(d, J = 7.47 Hz, 2H). MASS: 1004.18 |
| I.07 | 0.97(s, 3H), 1.11(s, 3H), 1.13(s, 3H), 1.24(s, 3H), 1.33(s, 9H), 1.40-1.49(m, 2H), 1.66-1.70(m, 5H), 1.76(s, 3H), 1.82-2.05(m, 2H), 1.98(s, 3H), 2.16-2.84(m, 10H), 2.46(s, 3H), 3.00(m, 1H), 3.95(d, J = 6.55 Hz, 1H), 4.20-4.35(m, 4H), 4.98(d, J = 7.94 Hz, 1H), 5.21-5.74(s, 5H), 6.25-6.27(m, 1H), 6.88(br-s, 1H), 7.30-7.33(m, 3H), 7.35-7.41(m, 2H), 7.51(t, J = 7.59 Hz, 2H), 7.61(t, J = 7.31 Hz, 1H), 8.12(d, J = 7.28 Hz, 2H). MASS: 1032.52 |
| I.08 | 1.13(s, 3H), 1.22(s, 3H), 1.60-1.67(m, 12H), 1.83-1.92(m, 6H), 2.04-2.38(m, 3H), 2.23(s, 3H), 2.42(s, 3H), 2.49-2.94(m, 8H), 3.79(d, J = 6.84 Hz, 1H), 4.19(d, J = 8.30 Hz, 1H), 4.31(d, J = 8.32 Hz, 1H), 4.41-4.43(m, 1H), 4.97(d, J = 8.75 Hz, 1H), 5.43(d, J = 3.61 Hz, 1H), 5.67(d, J = 6.86 Hz, 1H), 5.89-5.94(m, 2H), 6.20(m, 1H), 6.28(s, 1H), 7.30-7.34(m, 2H), 7.40-7.43(m, 6H), 7.49-7.64(m, 4H), 7.83(d, J = 7.41 Hz, 2H), 8.13(d, J = 7.42 Hz, 2H). MASS: 1084.5 |
| I.09 | 1.14(s, 3H), 1.24(s, 3H), 1.60-1.68(m, 6H), 1.68(s, 3H), 1.80-2.04(m, 3H), 2.23(s, 3H), 2.15-2.77(m, 7H), 2.48(s, 3H), 3.82(d, J = 6.85 Hz, 1H), 4.20(d, J = 8.18 Hz, 1H), 4.33(d, J = 8.52 Hz, 1H), 4.45(m, 1H), 4.98(d, J = 9.15 Hz, 1H), 5.53-5.55 (m, 1H), 5.69(d, J = 7.09 Hz, 1H), 6.00(dd, J$_1$ = 9.10 Hz, J$_2$ = 2.79 Hz, 1H), 6.23-6.51(m, 2H), 6.73-7.16(m, 2H), 7.34-7.66 (m,10H), 7.70(s, 1H), 7.75(dd, J$_1$ = 8.4 Hz, J$_2$ = 1.61 Hz, 2H), 8.12-8.16(m, 2H). MASS: 1034.61 |
| I.10 | 1.13(s, 3H), 1.22(s, 3H), 1.60-1.67(m, 12H), 1.83-1.92(m, 6H), 2.04-2.38(m, 3H), 2.23(s, 3H), 2.42(s, 3H), 2.49-2.94(m, 8H), 3.79(d, J = 6.84 Hz, 1H), 4.19(d, J = 8.30 Hz, 1H), 4.31(d, J = 8.32 Hz, 1H), 4.41-4.43(m, 1H), 4.97(d, J = 8.75 Hz, 1H), 5.43(d, J = 3.61 Hz, 1H), 5.67(d, J = 6.86 Hz, 1H), 5.89-5.94(m, 2H), 6.20(m, 1H), 6.28(s, 1H), 7.30-7.34(m, 2H), 7.40-7.43(m, 6H), 7.49-7.64(m, 4H), 7.83(d, J = 7.41 Hz, 2H), 8.13(d, J = 7.42 Hz, 2H), MASS: 1036.56 |

EXAMPLE 5

Conversion of Compound of Formula I to the Active Taxane Compound in Human Plasma The conversion of the test compound I.04 of the present invention to the active/parent taxane compound was determined in the human plasma sample. The test compound of 2000 ng per nil concentration was added to human plasma at ambient temperature and was kept in an incubator maintained at 37° C. Aliquots of this plasma sample were taken at definite time intervals and subjected to LC-MS/MS analysis. The samples were analyzed for amount of unconverted test compound and the amount of docetaxel formed in the test solution using LC-MS/MS operating in selected reaction monitoring (SRM) mode, as per follows:

Column: Hypurity Aquastar C-18, 50×2.1 mm, 3 micron

Mobile Phase: 10 mmol ammonium acetate-acetonitrile, 40:60

Flow Rate: 250 μl/min

Oven Temperature: 45° C.

Retention time of compound I.04: 13.9 min

Retention time of docetaxel: 0.79 min

The parent ions>product ions monitored were the following:

m/z 990.6>345.980 and m/z 990.6>182.366 (compound I.04) and m/z 830>247.866 and m/z 830>303.974 (for docetaxel)

Figure 2:
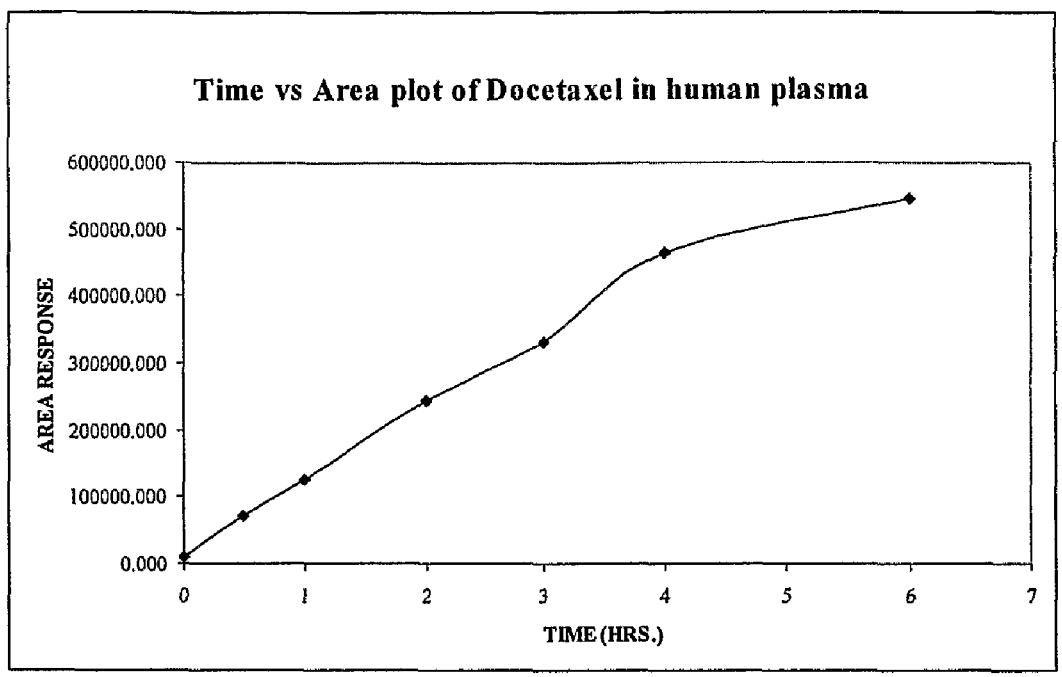
FIG. 2 depicts a time vs. area plot of docetaxel in human plasma.

The percentage of unconverted test compound I.04 measured at different time intervals is given in Table-3 below. The mass peak areas were also measured for the test compound I.04 and docetaxel, and are as given in Table-4. The time vs. area plots for the test compound and the released docetaxel are shown in FIGS. 1 and 2.

TABLE 3

| Time (hrs) | % Unconverted Compound I.04 |
|---|---|
| 0.0 | 100 |
| 0.5 | 59.1 |
| 1.0 | 40.3 |
| 2.0 | 4.7 |
| 4.0 | 0.1 |

TABLE 4

| Compound I.04 | | Docetaxel | |
|---|---|---|---|
| Time (hrs) | Peak Area (counts) | Time (hrs) | Peak Area (counts) |
| 0 | 24696932.5 | 0 | 10447.0 |
| 0.5 | 19303514.4 | 0.5 | 70713.8 |
| 1 | 16791382.3 | 1 | 125083.0 |
| 2 | 11789443.5 | 2 | 243846.6 |
| 3 | 6259891.0 | 3 | 331134.0 |
| 4 | 3007853.1 | 4 | 464924.3 |
| 6 | 904115.8 | 6 | 546298.2 |

As observed from the data in Table-3 and Table-4, and in FIGS. 1 and 2, the taxane conjugates of the present invention are converted to the active taxane compound under physiological conditions. The compounds of the present invention thus are potentially useful in the treatment of cancer.

EXAMPLE 6

Procedure for Testing Solubility of the Taxane Conjugates of Formula I

About 2 mg of the taxane conjugate of formula I was dispersed in 0.5 ml water (sterile) and sonicated for about 2 min. Small aliquots of a pharmaceutically accepted acid was added, sonicated for 2-3 min after each addition and observed for visual clarity.

For example, 2 mg of compound I.03 was dispersed in 0.5 ml water and sonicated for about 2 min. Added 20 μl of 2.5M HCl and sonicated for about 2 min 2000 ng per ml concentration to obtain a clear solution.

Under the above test conditions, both paclitaxel and docetaxel were completely insoluble.

The invention claimed is:

1. Compounds of formula I or salts thereof,

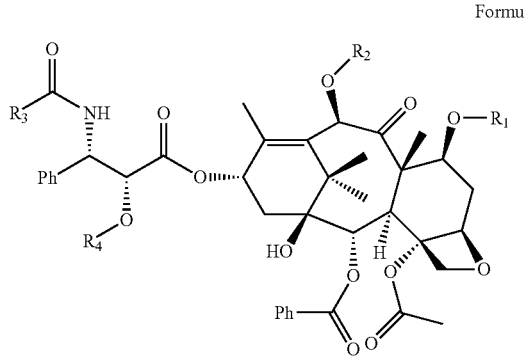

Formula I wherein, $R_1$ is selected from the group consisting of hydrogen and $R_4$;

$R_2$ is selected from the group consisting of hydrogen, acetyl and $R_4$;

$R_3$ is selected from the group consisting of alkyl, —O-alkyl, —NH-alkyl, aryl and heterocyclyl;

$R_4$ represents a moiety (A)

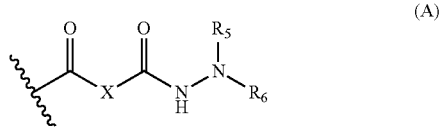

(A)

wherein, X is selected from the group consisting of a single bond, alkylene, alkenylene, alkynylene, arylene or a heterocyclylene moiety;

$R_5$ and $R_6$ are same or different and are independently selected from hydrogen, alkyl, aryl or heterocyclyl;

or $R_5$ and $R_6$ may form together with the nitrogen atom to which they are attached a heterocyclyl ring system.

2. A compound as claimed in claim 1 wherein $R_1$ is hydrogen, $R_2$ is selected from hydrogen and acetyl and $R_3$ is selected from phenyl and tert-butyloxy.

3. A compound as claimed in claim 1 selected from the group consisting of

2'-[N—(N,N-Dimethylamino) succinamidoyl]taxol;

10-Deacetyl-N-debenzoyl-N-(tent-butyloxycarbonyl)-2'-[(N-morpholin-4-yl)succinamidoyl]taxol;

10-Deacetyl-N-debenzoyl-N-(tert-butyloxycarbonyl)-2',7-bis[(N-piperidin-1-yl)succinamidoyl]taxol;

10-Deacetyl-N-debenzoyl-N-(tert-butyloxycarbonyl)-2'-[(N-piperidin-1-yl)succinamidoyl]taxol;

10-Deacetyl-N-debenzoyl-N-(tert-butyloxycarbonyl)-2'-[[5-methyl-3-(piperidin-1-ylcarbamoyemethyl]hexanoyl]taxol;

10-Deacetyl-N-debenzoyl-N-(tert-butyloxycarbonyl)-2'-[4-(piperidin-1-ylcarbamoyl)butyryl]taxol;

10-Deacetyl-N-debenzoyl-N-(tert-butyloxycarbonyl)-2'-[3,3-dimethyl-4-(piperidin-1-ylcarbamoyl)butyryl]taxol;

2'-[3-(N-(piperidin-1-yl)-carbamoyl)benzoyl]taxol;

2'-[(Z)-3-(Piperidin-1-ylcarbamoyl)acroyl]taxol;

2'-[(N-Piperidin-1-yl)succinamidoyl]taxol;

as well as their pharmaceutically acceptable salts.

4. A process for preparation of the compounds of the formula I, comprising, reacting the compound of formula II with a compound of formula III wherein $R_1, R_2, R_3, R_4, R_5, R_6$ and X are as defined for formula I and Y is a leaving group,

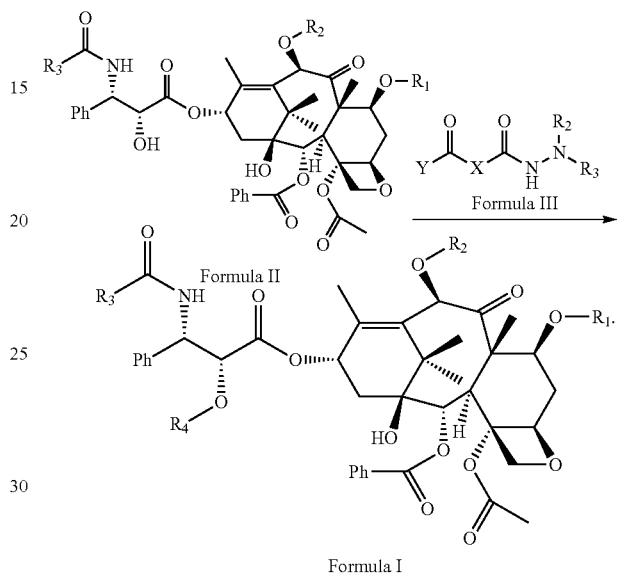

5. A process for preparation of the compounds of the formula I, comprising, reacting the compound of formula IV with a compound of formula V wherein $R_1, R_2, R_3, R_4, R_5, R_6$ and X are as defined for formula I and Y is a leaving group

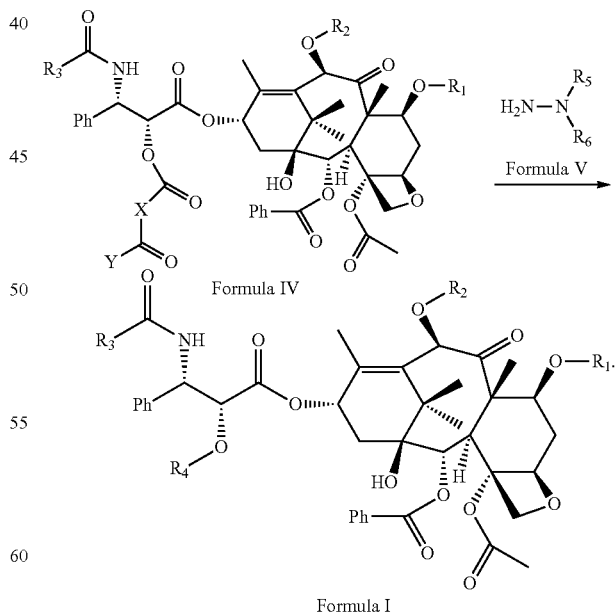

6. A method of treating tumors comprising administering an effective amount of compound of formula I as claimed in claim 1.

* * * * *

UNITED STATES PATENT AND TRADEMARK OFFICE
CERTIFICATE OF CORRECTION

PATENT NO. : 8,133,888 B2
APPLICATION NO. : 12/918985
DATED : March 13, 2012
INVENTOR(S) : Jiten R. Patel et al.

It is certified that error appears in the above-identified patent and that said Letters Patent is hereby corrected as shown below:

In column 27, line 64, in Claim 3, delete "ylcarbamoyemethyl]" and insert -- ylcarbamoyl)methyl] --, therefor.

In column 28, line 11, in Claim 4, delete "group," and insert -- group --, therefor.

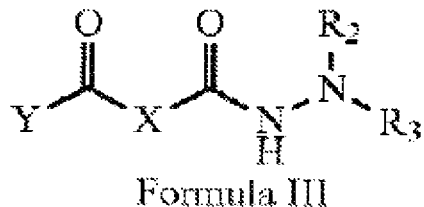

In column 28, lines 16-20, in Claim 4, delete " 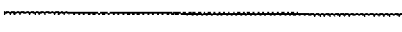 " and

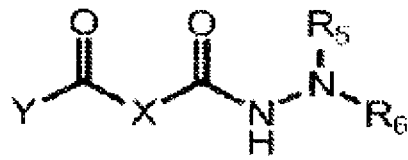

insert --  --, therefor.

Signed and Sealed this
Second Day of October, 2012

David J. Kappos
*Director of the United States Patent and Trademark Office*